(12) United States Patent
Mitchell et al.

(10) Patent No.: US 7,655,034 B2
(45) Date of Patent: Feb. 2, 2010

(54) STENT-GRAFT WITH ANCHORING PINS

(75) Inventors: James Mitchell, Windsor, CA (US);
Matthew Rust, Santa Rosa, CA (US);
Trevor Greenan, Santa Rosa, CA (US);
Frank Yang, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 336 days.

(21) Appl. No.: 11/559,765

(22) Filed: Nov. 14, 2006

(65) Prior Publication Data

US 2008/0114443 A1 May 15, 2008

(51) Int. Cl.
*A61F 2/06* (2006.01)
(52) U.S. Cl. .................................................. 623/1.15
(58) Field of Classification Search ........ 623/1.11–1.36
See application file for complete search history.

(56) References Cited

U.S. PATENT DOCUMENTS

| | | | |
|---|---|---|---|
| 4,140,126 A | 2/1979 | Choudhury | |
| 5,207,695 A | 5/1993 | Trout, III | |
| 5,391,172 A | 2/1995 | Williams et al. | |
| 5,397,355 A | 3/1995 | Marin et al. | |
| 5,489,295 A | 2/1996 | Piplani et al. | |
| 5,562,726 A | 10/1996 | Chuter | |
| 5,562,728 A * | 10/1996 | Lazarus et al. | 623/1.14 |
| 5,630,829 A | 5/1997 | Lauterjung | |
| 5,681,346 A | 10/1997 | Orth et al. | |
| 5,720,776 A | 2/1998 | Chuter et al. | |
| 5,733,325 A * | 3/1998 | Robinson et al. | 623/1.11 |
| 5,824,041 A | 10/1998 | Lenker et al. | |
| 5,843,167 A * | 12/1998 | Dwyer et al. | 623/1.14 |
| 5,855,601 A | 1/1999 | Bessler et al. | |
| 5,902,334 A | 5/1999 | Dwyer et al. | |
| 5,919,204 A | 7/1999 | Lukic et al. | |
| 6,004,347 A * | 12/1999 | McNamara et al. | 623/23.64 |
| 6,077,297 A | 6/2000 | Robinson et al. | |
| 6,245,101 B1 | 6/2001 | Drasler et al. | |
| 6,254,632 B1 | 7/2001 | Wu et al. | |
| 6,287,335 B1 | 9/2001 | Drasler et al. | |
| 6,312,462 B1 | 11/2001 | McDermott et al. | |
| 6,319,276 B1 | 11/2001 | Holman et al. | |

(Continued)

FOREIGN PATENT DOCUMENTS

| | | |
|---|---|---|
| FR | 2779939 | 6/1998 |
| WO | WO01/17458 | 3/2001 |
| WO | WO03/053288 | 7/2003 |
| WO | WO2006/086313 | 8/2006 |

OTHER PUBLICATIONS

U.S. Appl. No. 11/559,754, Nov. 14, 2006, Mitchell et al.

*Primary Examiner*—Suzette J Gherbi
(74) *Attorney, Agent, or Firm*—Serge Hodgson (57) ABSTRACT

A proximal anchor stent ring of an endoprosthesis includes proximal apexes, distal apexes, struts extending between the proximal apexes and the distal apexes, and anchor pins. The struts, the proximal apexes, and the distal apexes define an imaginary cylindrical surface. A pair of the anchor pins is located on the struts adjacent each of the proximal apexes, the anchor pins extending inwards from inside surfaces of the struts and protruding from the struts radially outward from the cylindrical surface. By locating the anchor pins inwards, the delivery profile of the proximal anchor stent ring is minimized.

25 Claims, 10 Drawing Sheets

U.S. PATENT DOCUMENTS

| | | |
|---|---|---|
| 6,395,017 B1 | 5/2002 | Dwyer et al. |
| 6,395,019 B2 | 5/2002 | Chobotov |
| 6,517,573 B1 | 2/2003 | Pollock et al. |
| 6,858,034 B1 | 2/2005 | Hijkema et al. |
| 6,890,337 B2 | 5/2005 | Feeser et al. |
| 7,004,964 B2 | 2/2006 | Thompson et al. |
| 7,147,661 B2 * | 12/2006 | Chobotov et al. .......... 623/1.16 |
| 7,175,652 B2 * | 2/2007 | Cook et al. ................ 623/1.13 |
| 2002/0116048 A1 | 8/2002 | Chobotov |
| 2003/0125797 A1 | 7/2003 | Chobotov et al. |
| 2003/0135162 A1 | 7/2003 | Deyette et al. |
| 2003/0158595 A1 | 8/2003 | Randall et al. |
| 2004/0088044 A1 | 5/2004 | Brown et al. |
| 2004/0093063 A1 | 5/2004 | Wright et al. |
| 2007/0250151 A1 | 10/2007 | Pereira |
| 2008/0114442 A1 * | 5/2008 | Mitchell et al. ............ 623/1.13 |

* cited by examiner

STENT-GRAFT WITH ANCHORING PINS

BACKGROUND OF THE INVENTION

1. Field of the Invention

This invention relates generally to medical devices and procedures, and more particularly to a method and system of deploying a stent-graft in a vascular system and to the associated stent-graft.

2. Description of the Related Art

Prostheses for implantation in blood vessels or other similar organs of the living body are, in general, well known in the medical art. For example, prosthetic vascular grafts formed of biocompatible materials (e.g., Dacron or expanded, porous polytetrafluoroethylene (PTFE) tubing) have been employed to replace or bypass damaged or occluded natural blood vessels.

A graft material supported by a framework is known as a stent-graft or endoluminal graft. In general, the use of stent-grafts for treatment or isolation of vascular aneurysms and vessel walls which have been thinned or thickened by disease (endoluminal repair or exclusion) is well known.

Many stent-grafts, are "self-expanding", i.e., inserted into the vascular system in a compressed or contracted state, and permitted to expand upon removal of a restraint. Self-expanding stent-grafts typically employ a wire or tube configured (e.g., bent or cut) to provide an outward radial force and employ a suitable elastic material such as stainless steel or Nitinol (nickel-titanium). Nitinol may additionally employ shape memory properties.

The self-expanding stent-graft is typically configured in a tubular shape of a slightly greater diameter than the diameter of the blood vessel in which the stent-graft is intended to be used. In general, rather than inserting in a traumatic and invasive manner, stents and stent-grafts are typically deployed through a less invasive intraluminal delivery, i.e., cutting through the skin to access a lumen or vasculature or percutaneously via successive dilatation, at a convenient (and less traumatic) entry point, and routing the stent-graft through the lumen to the site where the prosthesis is to be deployed.

Intraluminal deployment in one example is effected using a delivery catheter with coaxial inner tube, sometimes called the plunger, and outer tube, sometimes called the sheath, arranged for relative axial movement. The stent-graft is compressed and disposed within the distal end of the sheath in front of the inner tube.

The catheter is then maneuvered, typically routed though a lumen (e.g., vessel), until the end of the catheter (and the stent-graft) is positioned in the vicinity of the intended treatment site. The inner tube is then held stationary while the sheath of the delivery catheter is withdrawn. The inner tube prevents the stent-graft from moving back as the sheath is withdrawn.

As the sheath is withdrawn, the stent-graft is gradually exposed from a proximal end to a distal end of the stent-graft, the exposed portion of the stent-graft radially expands so that at least a portion of the expanded portion is in substantially conforming surface contact with a portion of the interior of the lumen, e.g., blood vessel wall.

The proximal end of the stent-graft is the end closest to the heart whereas the distal end is the end furthest away from the heart during deployment. In contrast and of note, the distal end of the catheter is usually identified to the end that is farthest from the operator (handle) while the proximal end of the catheter is the end nearest the operator (handle). For purposes of clarity of discussion, as used herein, the distal end of the catheter is the end that is farthest from the operator (the end furthest from the handle) while the distal end of the stent-graft is the end nearest the operator (the end nearest the handle), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the stent-graft and delivery system description may be consistent or opposite in actual usage.

Many self expanding stent-graft deployment systems are configured to have the proximal end of the stent-graft deploy as the sheath is pulled back. The proximal end of the stent-graft is typically designed to fixate and seal the stent-graft to the wall of the vessel during deployment. Such a configuration leaves little room for error in placement since re-positioning the stent-graft after initial deployment, except for a minimal pull down retraction, is usually difficult if possible at all. Deploying the proximal end of the stent-graft first makes accurate pre-deployment positioning of the stent-graft critical.

Attempts to overcome this problem generally fail to provide adequate control in manipulating the stent-graft positioning in both the initial deployment of the stent-graft and the re-deployment of the stent-graft (once the stent-graft has been partially deployed).

Another problem encountered with existing systems, particularly with systems that have a distal end of a stent-graft fixed during deployment (or during the uncovering of the sheath) is the frictional forces that can cause the stent-graft to axially compress or bunch up as the sheath is retracted. This bunching increases the density of the stent-graft within the sheath and can further increase the frictional drag experienced during deployment.

SUMMARY OF THE INVENTION

A delivery system for an endoprosthesis includes a spindle having a spindle body and spindle pins extending radially outward from the spindle body. The delivery system further includes a tapered tip having a sleeve, the spindle pins extending from the spindle body toward the sleeve. The endoprosthesis includes a proximal anchor stent ring having spindle pin catches and anchor pins. The spindle pins of the spindle extend into the spindle pin catches and the sleeve radially constrains the anchor pins.

A method of deploying the endoprosthesis includes radially constraining the proximal anchor stent ring of the endoprosthesis in an annular space between the sleeve of the tapered tip and the spindle. The method further includes radially constraining a graft material of the endoprosthesis in a primary sheath, the graft material being attached to a distal end of the proximal anchor stent ring. By radially constraining the graft material of the endoprosthesis by the primary sheath and radially constraining the proximal anchor stent ring by the sleeve, sequential and independent deployment of the graft material and the proximal anchor stent ring is facilitated.

The primary sheath is retracted to deploy a portion of the endoprosthesis. As the endoprosthesis is only partially deployed and the proximal anchor stent ring is radially constrained and un-deployed, the endoprosthesis can be repositioned in the event that the initial positioning of the endoprosthesis is less than desirable.

Further, as the proximal end of the endoprosthesis is secured and, in one example, the distal end is free to move within the primary sheath, bunching of the endoprosthesis during retraction of the primary sheath is avoided. By avoiding bunching, frictional drag of the endoprosthesis on the primary sheath during retraction is minimized thus facilitating smooth and easy retraction of the primary sheath.

Once the endoprosthesis is properly positioned, the tapered tip is advanced to deploy the proximal anchor stent ring thus anchoring the endoprosthesis in position within the vessel. The anchor pins of the proximal anchor stent ring protrude radially outward and penetrate into the vessel wall, e.g., into healthy strong tissue.

In accordance with one example, the proximal anchor stent ring of the endoprosthesis includes proximal apexes, distal apexes, and struts extending between the proximal apexes and the distal apexes. The struts, the proximal apexes, and the distal apexes define a cylindrical surface. A pair of the anchor pins is located on the struts adjacent each of the proximal apexes, the anchor pins extending inwards (relative to the curve of the proximal apexes) from inside surfaces of the struts and protruding from the struts radially outward from the cylindrical (outer circumferential) surface.

By locating the anchor pins inwards, the delivery profile, sometimes called crimped profile, of the proximal anchor stent ring is minimized.

These and other features according to the present invention will be more readily apparent from the detailed description set forth below taken in conjunction with the accompanying drawings.

BRIEF DESCRIPTION OF THE DRAWINGS

In the following description, the same or similar elements are labeled with the same or similar reference numbers.

DETAILED DESCRIPTION

Figure 1:
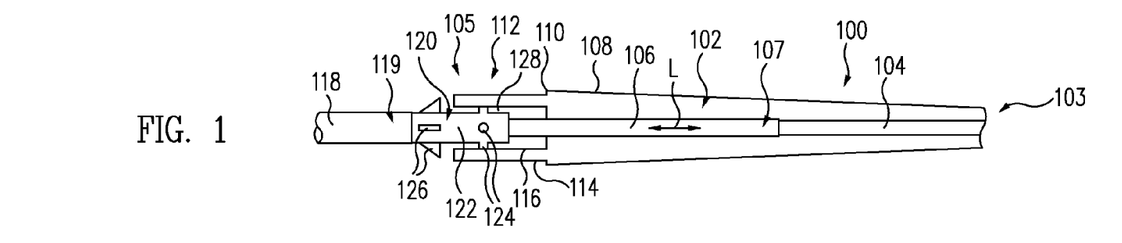
FIG. 1 is a partial cross-sectional view of a stent-graft delivery system without a stent-graft and outer sheath in accordance with one embodiment.

FIG. 1 is a partial cross-sectional view of a stent-graft delivery system 100 without a stent-graft and outer sheath in accordance with one embodiment. Stent-graft delivery system 100 includes a tapered tip 102 that is flexible and able to provide trackability in tight and tortuous vessels. Tapered tip 102 includes a guidewire lumen 104 therein for connecting to adjacent members and allowing passage of a guidewire through tapered tip 102. Other tip shapes such as bullet-shaped tips could also be used.

An inner tube 106 defines a lumen, e.g., a guide wire lumen, therein. A distal end 107 of inner tube 106 is located within and secured to tapered tip 102, i.e., tapered tip 102 is mounted on inner tube 106. As shown in FIG. 1, the lumen of inner tube 106 is in fluid communication with guidewire lumen 104 of tapered tip 102 such that a guide wire can be passed through inner tube 106 and out distal end 107, through guidewire lumen 104 of tapered tip 102, and out a distal end 103 of tapered tip 102.

Tapered tip 102 includes a tapered outer surface 108 that gradually increases in diameter. More particularly, tapered outer surface 108 has a minimum diameter at distal end 103 and gradually increases in diameter proximally, i.e., in the direction of the operator (or handle of stent-graft delivery system 100), from distal end 103.

Tapered outer surface 108 extends proximally to a primary sheath abutment surface (shoulder) 110 of tapered tip 102. Primary sheath abutment surface 110 is an annular ring perpendicular to a longitudinal axis L of stent-graft delivery system 100.

Tapered tip 102 further includes a (tip) sleeve 112 extending proximally from primary sheath abutment surface 110. Generally, sleeve 112 is at a proximal end 105 of tapered tip 102. Sleeve 112 is a hollow cylindrical tube extending proximally and longitudinally from primary sheath abutment surface 110. Sleeve 112 includes an outer cylindrical surface 114 and an inner cylindrical surface 116.

Stent-graft delivery system 100 further includes an outer tube 118 having a spindle 120 located at and fixed to a distal end 119 of outer tube 118. Spindle 120 includes a spindle body 122 having a cylindrical outer surface, a plurality of spindle pins 124 protruding radially outward from spindle body 122, and a plurality of primary sheath guides 126 protruding radially outward from spindle body 122. Primary sheath guides 126 guide the primary sheath into position over (tip) sleeve 112 (see FIG. 2 for example).

As illustrated in FIG. 1, spindle 120 is configured to slip inside of sleeve 112 such that spindle pins 124 are directly adjacent to, or contact, inner cylindrical surface 116 of sleeve 112. Spindle pins 124 extend from spindle body 122 towards and to sleeve 112. Generally, the diameter to which spindle pins 124 extend from spindle body 112 is approximately equal to, or slightly less than, the diameter of inner cylindrical surface 116 of sleeve 112 allowing spindle pins 124 to snugly fit inside of sleeve 112. An annular space 128 exists between inner cylindrical surface 116 and spindle body 122.

Inner tube 106 is within and extends through outer tube 118 and spindle 120. Inner tube 106 and thus tapered tip 102 is moved along longitudinal axis L (longitudinally moved) relative to outer tube 118 and thus spindle 120 to release the proximal end of a stent-graft as discussed further below. The term "stent-graft" used herein should be understood to include stent-grafts and other forms of endoprosthesis.

Figure 2:
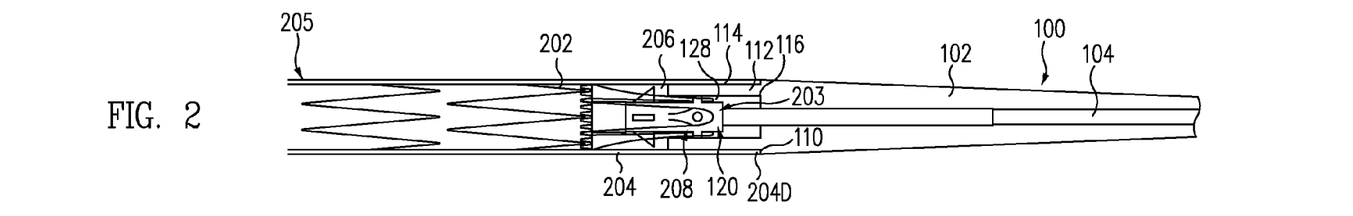
FIG. 2 is a partial cross-sectional view of the stent-graft delivery system of FIG. 1 including a stent-graft located within a retractable primary sheath in a pre-deployment un-retracted position.

FIG. 2 is a partial cross-sectional view of the stent-graft delivery system 100 of FIG. 1 including a stent-graft 202 located within a retractable primary sheath 204 in a pre-deployment un-retracted position.

Primary sheath 204 is a hollow tube and defines a lumen 206 therein through which outer tube 118 and inner tube 106 extend. Primary sheath 204 is in a pre-deployment un-retracted position in FIG. 2. Primary sheath 204 is moved proximally along longitudinal axis L, sometimes called retracted, relative to outer tube 118/spindle 120 and thus stent-graft 202 to deploy a portion of stent-graft 202 as discussed further below. In one embodiment, stent-graft 202 is a self-expanding stent-graft such that stent-graft 202 self-expands upon being released from its radially constrained position. In accordance with this example, stent-graft 202 includes a graft material and support structures attached to the graft material as discussed in greater detail below with reference to FIG. 5. Stent-graft 202 includes a proximal end 203 and a distal end 205.

As shown in FIG. 2, stent-graft 202 is in a radially constrained configuration over outer tube 118 and spindle 120. Stent-graft 202 is located within and radially compressed by primary sheath 204. Further, a proximal anchor stent ring 208, sometimes called the proximal tip, of stent-graft 202 is radially constrained and held in position in annular space 128 between spindle body 122 and inner cylindrical surface 116 of sleeve 112. Proximal anchor stent ring 208 is at proximal end 203 of stent-graft 202.

Generally, the graft material of stent-graft 202 is radially constrained by primary sheath 204 and the proximal portion of proximal anchor stent ring 208 is radially constrained by sleeve 112 allowing sequential and independent deployment of the graft material and proximal anchor stent ring 208 of stent-graft 202.

Primary sheath 204 includes a distal end 204D adjacent to or in abutting contact with primary sheath abutment surface 110 of tapered tip 102. Distal end 204D fits snugly around sleeve 112 and in one example lightly presses radially inward on outer cylindrical surface 114 of sleeve 112.

Figure 3:
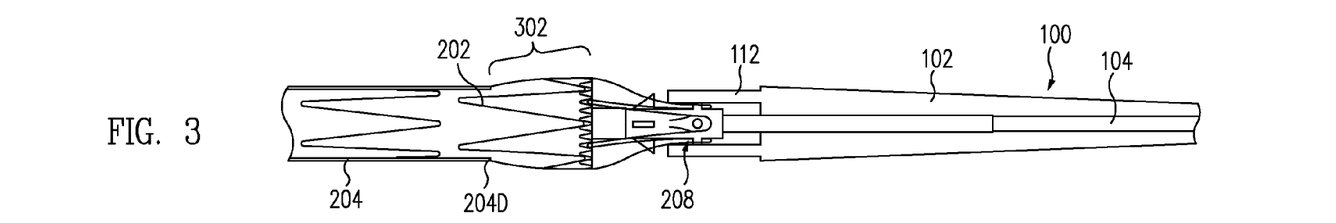
FIG. 3 is a partial cross-sectional view of the stent-graft delivery system of FIG. 2 with the retractable primary sheath partially retracted.

FIG. 3 is a partial cross-sectional view of the stent-graft delivery system 100 of FIG. 2 with retractable primary sheath 204 partially retracted. Referring now to FIG. 3, primary sheath 204 is partially retracted such that distal end 204D is spaced apart from tapered tip 102. Further, due to the retraction of primary sheath 204, a proximal portion 302 of stent-graft 202 is exposed and partially deployed. Proximal portion 302 is a portion of stent-graft 202 distal to proximal anchor stent ring 208 but proximal to the remaining portion of stent-graft 202.

As proximal portion 302 is only partially deployed and a portion of proximal anchor stent ring 208 is radially constrained and un-deployed, stent-graft 202 can be repositioned in the event that the initial positioning of stent-graft 202 is less than desirable. More particularly, to reposition stent-graft 202, the retraction of primary sheath 204 is halted. Stent-graft delivery system 100 is then moved to reposition stent-graft 202, for example, stent-graft 202 is rotated or moved proximally or distally without a substantial risk of damaging the wall of the vessel in which stent-graft 202 is being deployed.

Further, as proximal end 203 of stent-graft 202 is secured fixing proximal end 203 of stent-graft 202 and keeping it in tension as primary sheath 204 is retracted and, in one example, distal end 205 is free to move within primary sheath 204, bunching of stent-graft 202 during retraction of primary sheath 204 is avoided. By avoiding bunching, frictional drag of stent-graft 202 on primary sheath 204 during retraction is minimized thus facilitating smooth and easy retraction of primary sheath 204.

Once stent-graft 202 is properly position, proximal anchor stent ring 208 is released and deployed securing stent-graft 202 in position within the vessel as discussed in greater detail below.

Figure 4:
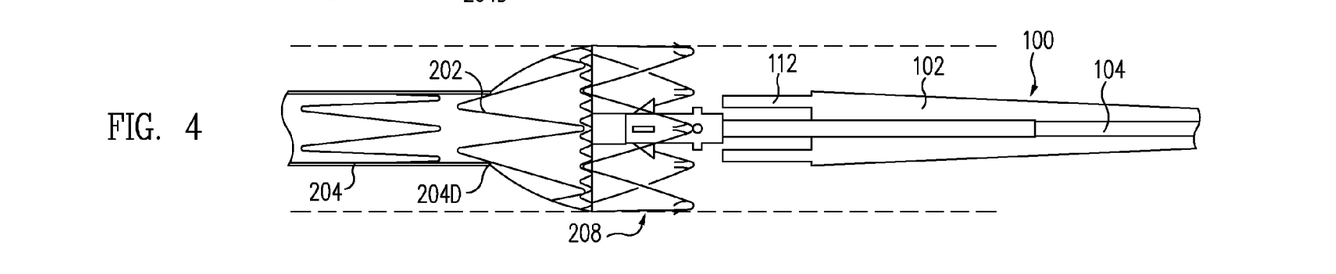
FIG. 4 is a partial cross-sectional view of the stent-graft delivery system of FIG. 3 after deployment of a proximal anchor stent ring of the stent-graft.

FIG. 4 is a partial cross-sectional view of the stent-graft delivery system 100 of FIG. 3 after deployment of proximal anchor stent ring 208 of stent-graft 202. Referring now to FIG. 4, tapered tip 102 is advanced relative to spindle 120 to expose the proximal end of proximal anchor stent ring 208. Upon being released from sleeve 112 of tapered tip 102, the proximal end of proximal anchor stent ring 208 self-expands into the wall of the vessel in which stent-graft 202 is being deployed.

As set forth below, proximal anchor stent ring 208 includes anchor pins which penetrate into the surrounding vessel wall thus anchoring proximal anchor stent ring 208 to the wall of the vessel. Accordingly, after deployment and anchoring of proximal anchor stent ring 208 to the vessel wall, primary sheath 204 is fully retracted to fully deploy stent-graft 202 without migration.

However, in another example, primary sheath 204 is fully retracted prior to release of proximal anchor stent ring 208. To illustrate, instead of being partially retracted at the stage of deployment illustrated in FIG. 3, primary sheath 204 is fully retracted while the proximal end of proximal anchor stent ring 208 is still radially constrained.

Further, stent-graft 202 is set forth above as being a self-expanding stent. In accordance with another embodiment, instead of being a self-expanding stent-graft, stent-graft delivery system 100 includes an expansion member, e.g., a balloon, which is expanded to expand and deploy the stent-graft.

Figure 5:
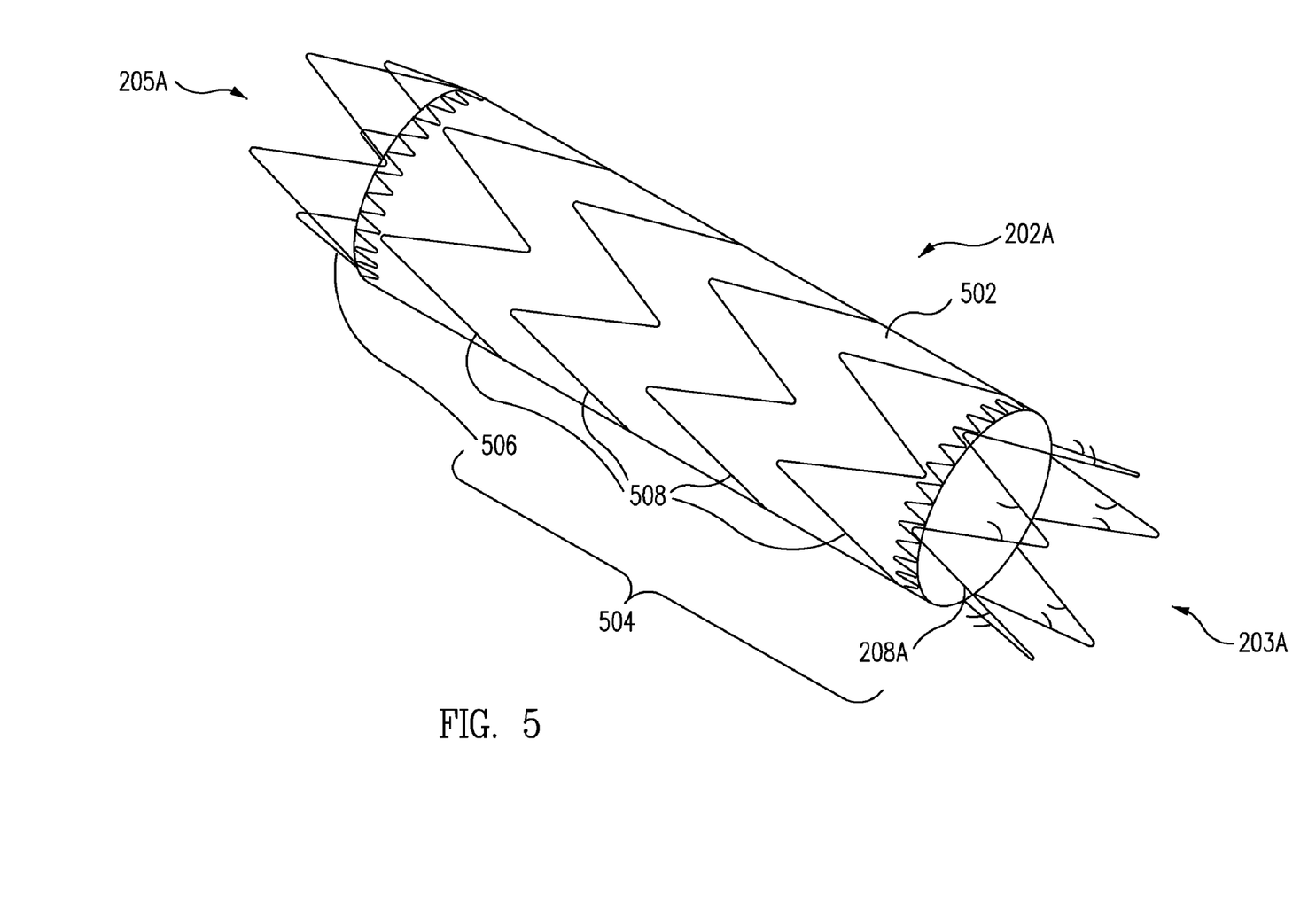
FIG. 5 is a perspective view of an expanded stent-graft similar to the stent-graft of FIGS. 2, 3 and 4.

FIG. 5 is a perspective view of an expanded stent-graft 202A similar to stent-graft 202 of FIGS. 2, 3 and 4. Referring now to FIG. 5, stent-graft 202A includes a graft material 502, e.g., formed of polyester or Dacron material, and a plurality of resilient self-expanding support structures 504, e.g., formed of super elastic self-expanding memory material such as Nitinol, including a proximal anchor stent ring 208A at a proximal end 203A, a distal stent ring 506 at a distal end 205A, and stent rings 508 between proximal anchor stent ring 208A and distal stent ring 506. Support structures 504 are attached to graft material 502, e.g., by sutures, adhesive, or other means.

Typically, stent-graft 202A is deployed such that graft material 502 spans, sometimes called excludes, a diseased portion of the vessel, e.g., an aneurysm. Further, proximal anchor stent ring 208A, e.g., a suprarenal stent structure, is typically engaged with a healthy portion of the vessel adjacent the diseased portion, the healthy portion having stronger tissue than the diseased portion. By forming proximal anchor stent ring 208A with anchor pins as discussed below, the anchor pins penetrate (land) into the vessel wall of the healthy tissue thus anchoring proximal anchor stent ring 208A to strong tissue.

Figure 6:
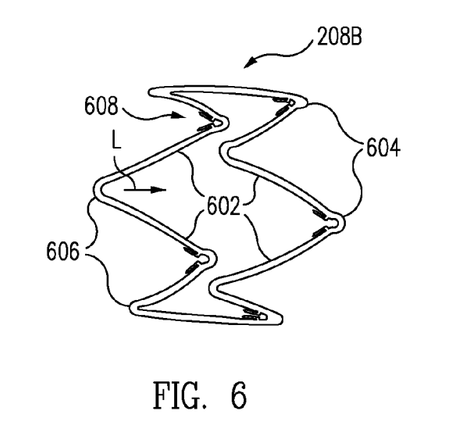
FIG. 6 is perspective view of an expanded proximal anchor stent ring similar to a proximal anchor stent ring of the stent-graft of FIG. 5.
Figure 7:
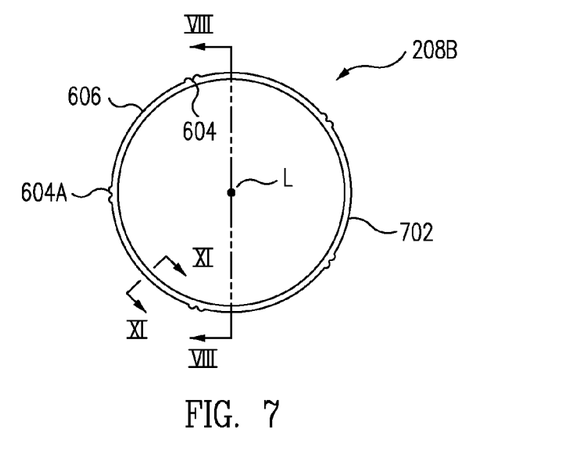
FIG. 7 is a top view of the proximal anchor stent ring of FIG. 6.
Figure 8:
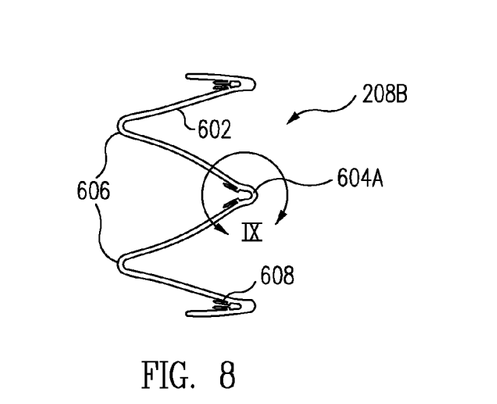
FIG. 8 is a cross-sectional view of the proximal anchor stent ring along the line VIII-VIII of FIG. 7.
Figure 9:
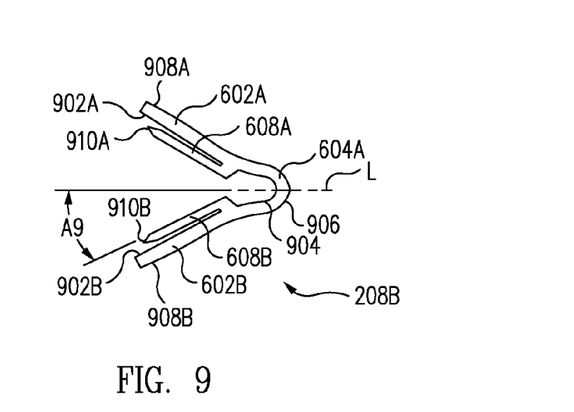
FIG. 9 is an enlarged view of a region IX of the proximal anchor stent ring of FIG. 8.
Figure 10:
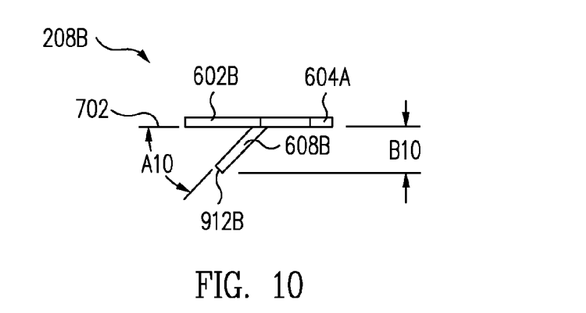
FIG. 10 is a side view of the region of the proximal anchor stent ring of FIG. 9.
Figure 11:
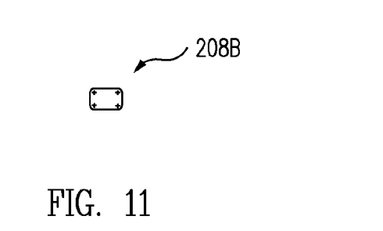
FIG. 11 is a cross-sectional view of the proximal anchor stent ring along the line XI-XI of FIG. 7.

FIG. 6 is perspective view of an expanded proximal anchor stent ring 208B similar to proximal anchor stent ring 208A of stent-graft 202A of FIG. 5. FIG. 7 is a top view of proximal anchor stent ring 208B of FIG. 6. FIG. 8 is a cross-sectional view of proximal anchor stent ring 208B along the line VIII-VIII of FIG. 7. FIG. 9 is an enlarged view of a region IX of proximal anchor stent ring 208B of FIG. 8. FIG. 10 is a side view of the region of proximal anchor stent ring 208B of FIG. 9. FIG. 11 is a cross-sectional view of proximal anchor stent ring 208B along the line XI-XI of FIG. 7.

Referring now to FIGS. 6, 7, 8, 9, 10, and 11 together, proximal anchor stent ring 208B includes a zigzag pattern of struts 602 alternating between proximal apexes 604 and distal apexes 606. Illustratively, proximal anchor stent ring 208B is laser cut from a one-piece material such as a tube. After being cut, proximal anchor stent ring 208B is sequentially expanded, e.g., using a mandrel, and heat set, into its final expanded configuration as those of skill in the art will understand in light of this disclosure. In one example, the mandrel includes protruding features which facilitate heat setting of the anchor pins in position.

Distal apexes 606 are attached to the graft material of the stent-graft, e.g., see graft material 502 of FIG. 5. Proximal anchor stent ring 208B further includes anchor pins 608.

More particularly, a pair of anchor pins 608 is located on struts 602 adjacent each proximal apex 604. By locating anchor pins 608 adjacent proximal apexes 604, the effect on the flexibility of proximal anchor stent ring 208B by anchor pins 608 is minimal. Further, as proximal anchor stent ring 208B is integral in one example, i.e., is a single piece laser cut from a tube and not a plurality of separate pieces attached together, anchor pins 608 are durable, e.g., are not likely to break off or otherwise fail.

Referring now to FIG. 9, a first proximal apex 604A of the plurality of proximal apexes 604 is illustrated. First and second struts 602A, 602B of the plurality of struts 602 extends distally from proximal apex 604A. A first anchor pin 608A of the plurality of anchor pins 608 extends from strut 602A adjacent proximal apex 604A. Similarly, a second anchor pin 608B of the plurality of anchor pins 608 extends from strut 602B adjacent proximal apex 604A and directly opposite first anchor pin 608A.

In one embodiment, the angle of anchor pins 608 from the vertical (horizontal in the view of FIG. 9) is in the range of 0° to 50°, e.g., feature A9 is in the range of 0° to 50° and in one example is 45°. By forming anchor pins 608 at an angle in the range of 0° to 50° from the vertical, anchor pins 608 are in line with any force for migration, e.g., force in the distal direction (force in the left direction in the view of FIG. 9). In one embodiment, the vertical is parallel to the longitudinal axis L of proximal anchor stent ring 208B.

Anchor pins 608A, 608B extend from the inside surfaces 902A, 902B of struts 602A, 602B, respectively. As used herein, the inside and outside surfaces of struts 602 are defined relative to proximal apexes 604. More particularly, the inside surface of a strut 602 is the surface that correlates and extends smoothly from the inside radial surface of the curved apex, i.e., the curvature of proximal apexes 604. Conversely, the outside surface of a strut 602 correlates to the outside radial surface of proximal apexes 604. Generally, the outside surfaces of struts 602 are proximal to the inside surfaces of struts 602.

To illustrate, proximal apex 604A includes an intrados (the interior curve of an arch) surface 904 and an extrados (the exterior curve of an arch) surface 906, extrados surface 906 having a greater radius then intrados surface 904. Extrados surface 906 is continuous with outside surfaces 908A, 908B of struts 602A, 602B, respectively. Similarly, intrados surface 904 is continuous with inside surfaces 902A, 902B of struts 602A, 602B, respectively. Stated another way, anchor pins 608A, 608B extend inwards from struts 602A, 602B, respectively.

Generally, anchor pins 608 are located inwards of struts 602. By locating anchor pins 608 inwards, the delivery profile, sometimes called crimped profile, of proximal anchor stent ring 208B is minimized in contrast to a configuration where anchor pins are located outward and space must be allocated to accommodate the anchor pins.

In accordance with this example, anchor pins 608 include distal tips, e.g., sharp points, which facilitate penetration of anchor pins 608 into the wall of the vessel in which the stent-graft is deployed. To illustrate, paying particular attention to FIG. 9, anchor pins 608A, 608B include distal tips 910A, 910B, respectively.

Further, anchor pins 608A, 608B protrude radially outward from the cylindrical surface (plane) defined by the zigzag pattern of struts 602 alternating between proximal apexes 604 and distal apexes 606. Generally, anchor pins 608A, 608B protrude radially outward from proximal anchor stent ring 208B.

Paying particular attention now to FIGS. 7 and 10, struts 602, proximal apexes 604, and distal apexes 606 define a cylindrical surface 702. Anchor pins 608 protrude from struts 602 radially outward from (imaginary) cylindrical surface 702. As discussed in greater detail below with reference to FIG. 13, by protruding radially outwards from proximal anchor stent ring 208B, anchor pins 608 penetrate into the vessel wall thus anchoring proximal anchor stent ring 208B and the corresponding stent-graft to the vessel wall.

Illustratively, anchor pins 608 protrude radially outward (the radial distance from the imaginary cylindrical surface 702 in contrast to the length of anchor pins 608) from struts 602 a distance in the range of one millimeter to three millimeters, i.e., feature B10 of FIG. 10 is 3 mm, in the range of 1 mm to 3 mm in one example, and in the range of 2 mm to 3 mm in another example. Further, feature A10, i.e., the angle of intersection between anchor pins 608 and struts 602 is 45° or in the range of 30° to 75° in one example. By forming the angle of intersection in the range of 30° to 75°, any force in the distal direction on proximal anchor stent ring 208B (left in the view of FIG. 10) causes anchor pins 608 to penetrate (dig) deeper into the vessel wall thus pulling struts 602 and proximal apexes 604 tighter to the vessel wall effectively locking proximal anchor stent ring 208B to the vessel wall.

Figure 12:
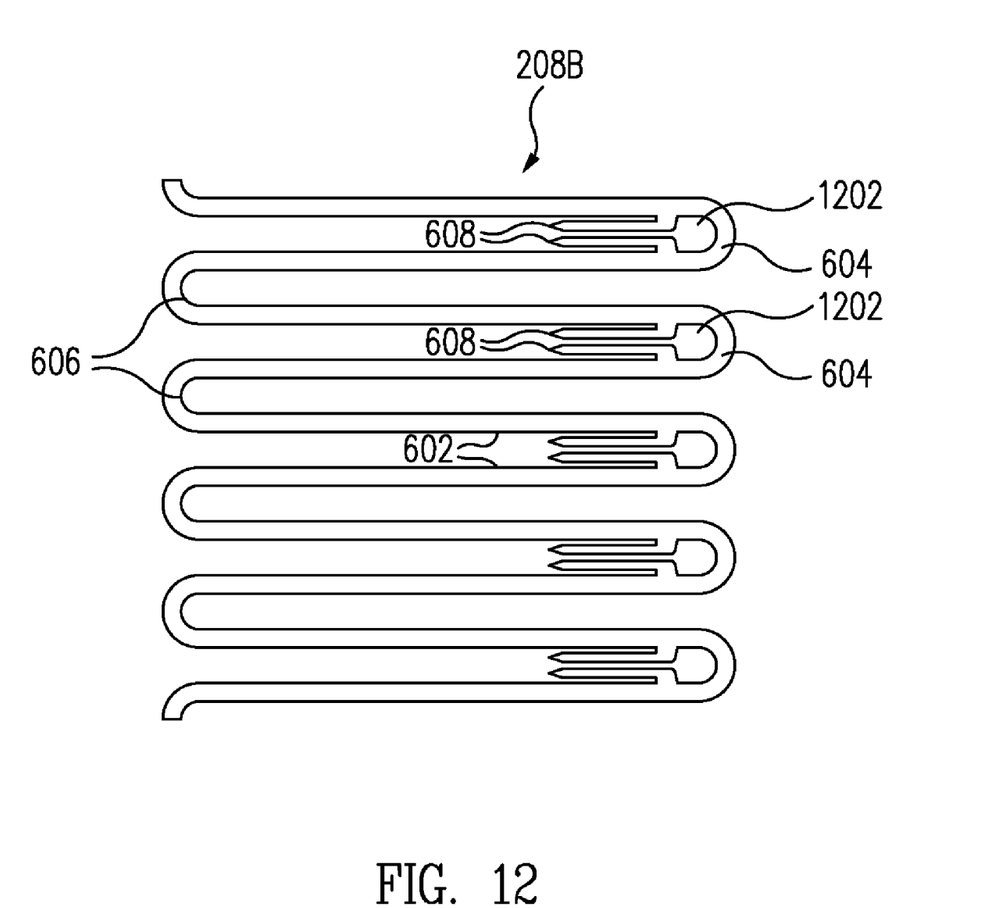
FIG. 12 is an a flattened pattern of the as cut proximal anchor stent ring of FIGS. 6-11.

FIG. 12 is an as cut flat pattern of proximal anchor stent ring 208B of FIGS. 6-11. Referring now to FIG. 12, proximal anchor stent ring 208B is illustrated in its unexpanded configuration, sometimes called delivery profile. In its unexpanded configuration, proximal apexes 604 and anchor pins 608 define spindle pin catches 1202.

Spindle pin catches 1202 are pockets, sometimes called openings or holes, in which the spindle pins of the stent-graft delivery system are located to radially constrain proximal anchor stent ring 208B in its unexpanded configuration (crimped profile) prior to deployment as discussed in greater detail below. Generally, anchor pins 608 are positioned slightly distal from proximal apexes 604 to leave room for the spindle pins.

Although proximal anchor stent ring 208B is illustrated as having five proximal apexes 604 and five distal apexes 606, sometimes called a five apex proximal anchor stent ring, in other examples, a proximal anchor stent ring has more or less than five proximal apexes and five distal apexes, e.g., four or six of each, sometimes called a four or six apex proximal anchor stent ring.

Figure 13:
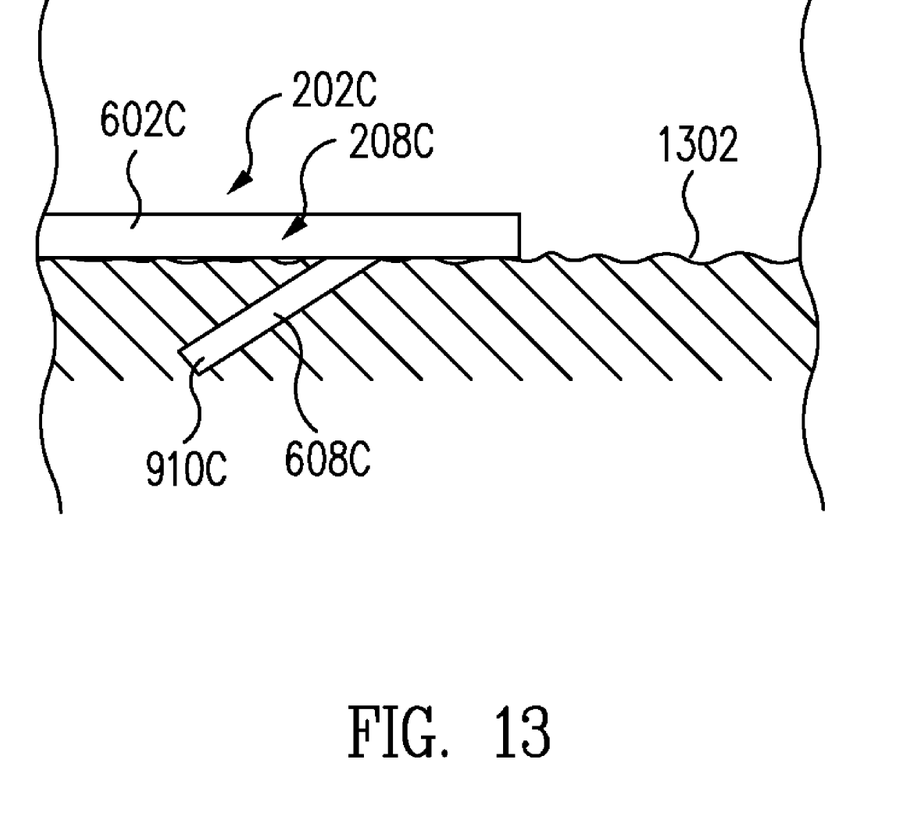
FIG. 13 is a partial cross-sectional view of a proximal anchor stent ring anchored in a vessel wall in accordance with one embodiment.

FIG. 13 is a partial cross-sectional view of a proximal anchor stent ring 208C of a stent-graft 202C anchored in a vessel wall 1302 in accordance with one embodiment. Referring now to FIG. 13, an anchor pin 608C is extending radially outward from a strut 602C and penetrating into vessel wall 1302. Distal tip 910C of anchor pin 608C facilitates penetration of anchor pin 608C into vessel wall 1302, e.g., healthy tissue. Accordingly, proximal anchor stent ring 208C is anchored to vessel wall 1302 preventing migration of stent-graft 202C in the distal direction, i.e., prevents motion of stent-graft 202C towards the left in the view of FIG. 13.

Figure 14:
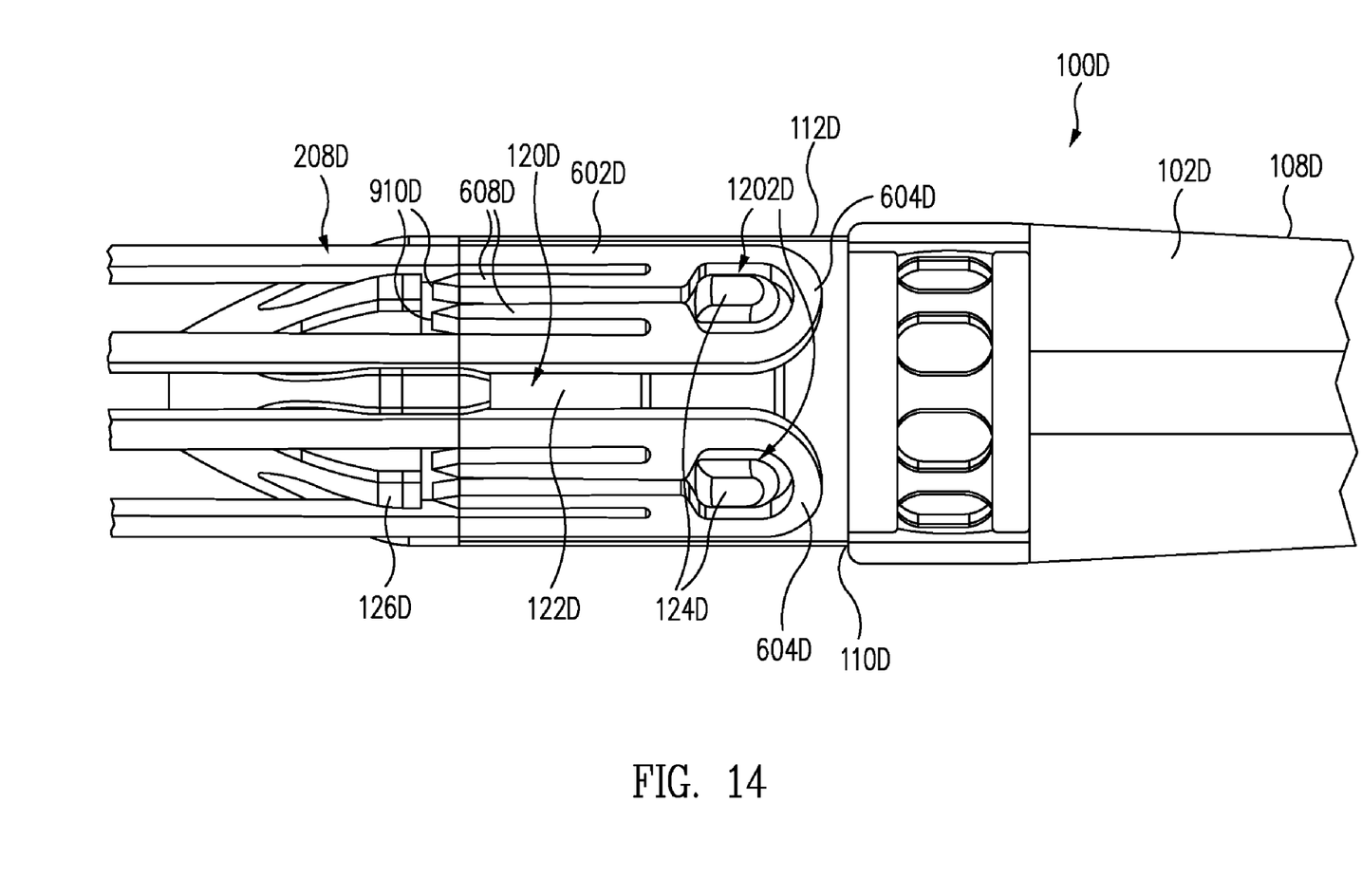
FIG. 14 is an enlarged partially cutaway view of a stent-graft delivery system in accordance with another embodiment.

FIG. 14 is an enlarged partially cutaway view of a stent-graft delivery system 100D in accordance with another embodiment. Referring now to FIG. 14, a proximal portion of proximal anchor stent ring 208D is restrained within a sleeve 112D of a tapered tip 102D. Sleeve 112D is illustrated as a transparent sleeve in FIG. 14 to illustrate features within sleeve 112D. However, in other examples, sleeve 112D is opaque. Illustratively, sleeve 112D is stainless steel, Nitinol, MP35N alloy, or a polymer.

Spindle pins 124D of a spindle 120D extend into and are located within spindle pin catches 1202D of proximal anchor stent ring 208D. Accordingly, the proximal end of proximal anchor stent ring 208D is locked around spindle pins 124D and between sleeve 112D and a spindle body 122D. Illustratively, spindle 120D is stainless steel, Nitinol, MP35N alloy, or a polymer.

Further, sleeve 112D holds anchor pins 608D down (radially inward) thus providing a minimal delivery profile for proximal anchor stent ring 208D. Generally, sleeve 112D holds anchor pins 608D bent in a lower profile.

Sleeve 112D does not cover (exposes) distal tips 910D of anchor pins 608D. Stated another way, sleeve 112D extends distally only partially over anchor pins 608D. This prevents distal tips 910D, e.g., sharp tips, from engaging (digging into, scratching, gouging) sleeve 112D. This minimizes the deployment force necessary to advance sleeve 112D relative to proximal anchor stent ring 208D.

Tapered outer surface 108D, primary sheath abutment surface 110D, primary sheath guides 126D, struts 602D, proximal apexes 604D are similar to tapered outer surface 108, primary sheath abutment surface 110, primary sheath guides 126, struts 602, proximal apexes 604 as discussed above, respectively, and so the description thereof is not repeated here.

Figure 15:
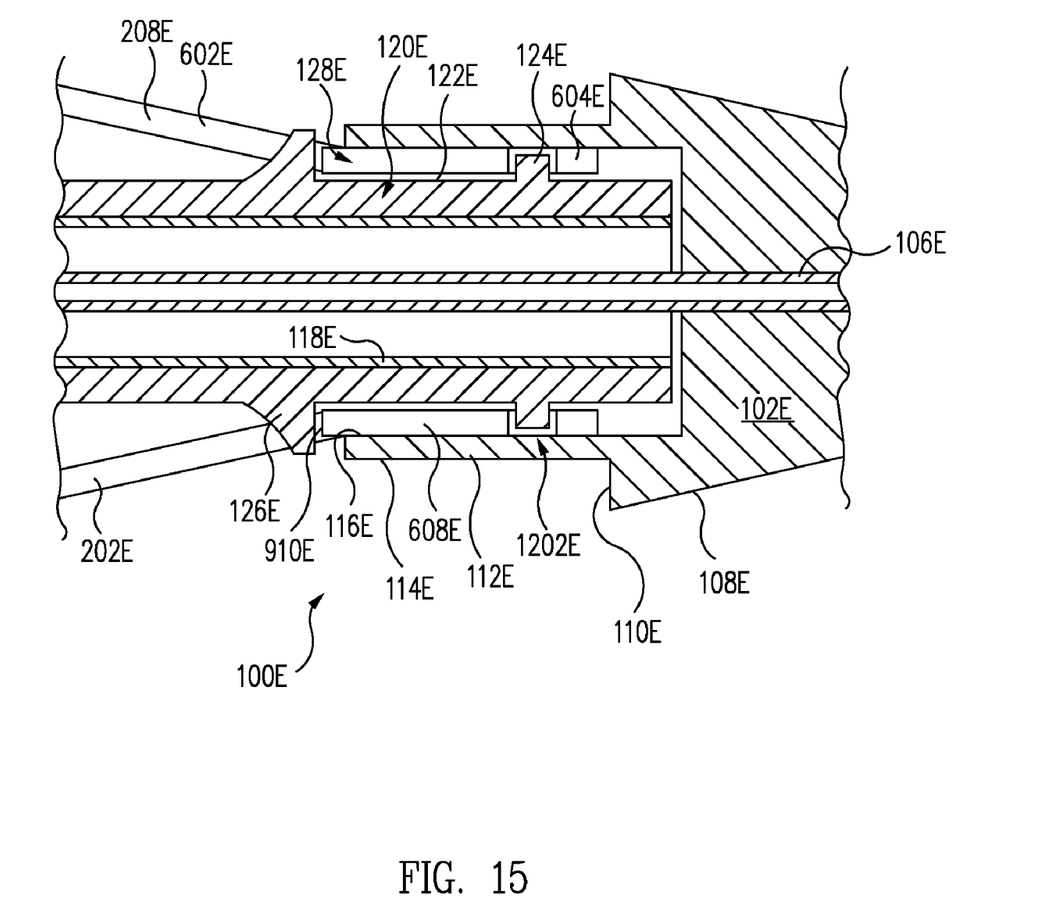
FIG. 15 is a cross-sectional view of a stent-graft delivery system in accordance with another embodiment.

FIG. 15 is a cross-sectional view of a stent-graft delivery system 100E in accordance with another embodiment. FIG. 15 corresponds to the stage similar to that illustrated in FIG. 3 of deployment of a stent-graft 202E, i.e., after at least partial retraction of the primary sheath.

Referring now to FIG. 15, stent-graft delivery system 100E includes a tapered tip 102E, an inner tube 106E, a tapered outer surface 108E, a primary sheath abutment surface 110E, a sleeve 112E, an outer cylindrical surface 114E, an inner cylindrical surface 116E, an outer tube 118E, a spindle 120E, a spindle body 122E, spindle pins 124E, primary sheath guides 126E, an annular space 128E similar to tapered tip 102, inner tube 106, tapered outer surface 108, primary sheath abutment surface 110, sleeve 112, outer cylindrical surface 114, inner cylindrical surface 116, outer tube 118, spindle 120, spindle body 122, spindle pins 124, primary sheath guides 126, annular space 128 of stent-graft delivery system 100 of FIGS. 1-4, respectively.

Further, stent-graft 202E includes a proximal anchor stent ring 208E including struts 602E, proximal apexes 604E, anchor pins 608E, distal tips 910E, and spindle pin catches 1202E similar to proximal anchor stent ring 208B including struts 602, proximal apexes 604, anchor pins 608, distal tips 910, and spindle pin catches 1202 of proximal anchor stent ring 208B of FIGS. 6-12, respectively.

As shown in FIG. 15, the proximal end of proximal anchor stent ring 208E is restrained within sleeve 112E of tapered tip 102E. Spindle pins 124E of spindle 120E are located within spindle pin catches 1202E of proximal anchor stent ring 208E. Accordingly, proximal anchor stent ring 208E is locked around spindle pins 124E and between sleeve 112E and a spindle body 122E.

Figure 16:
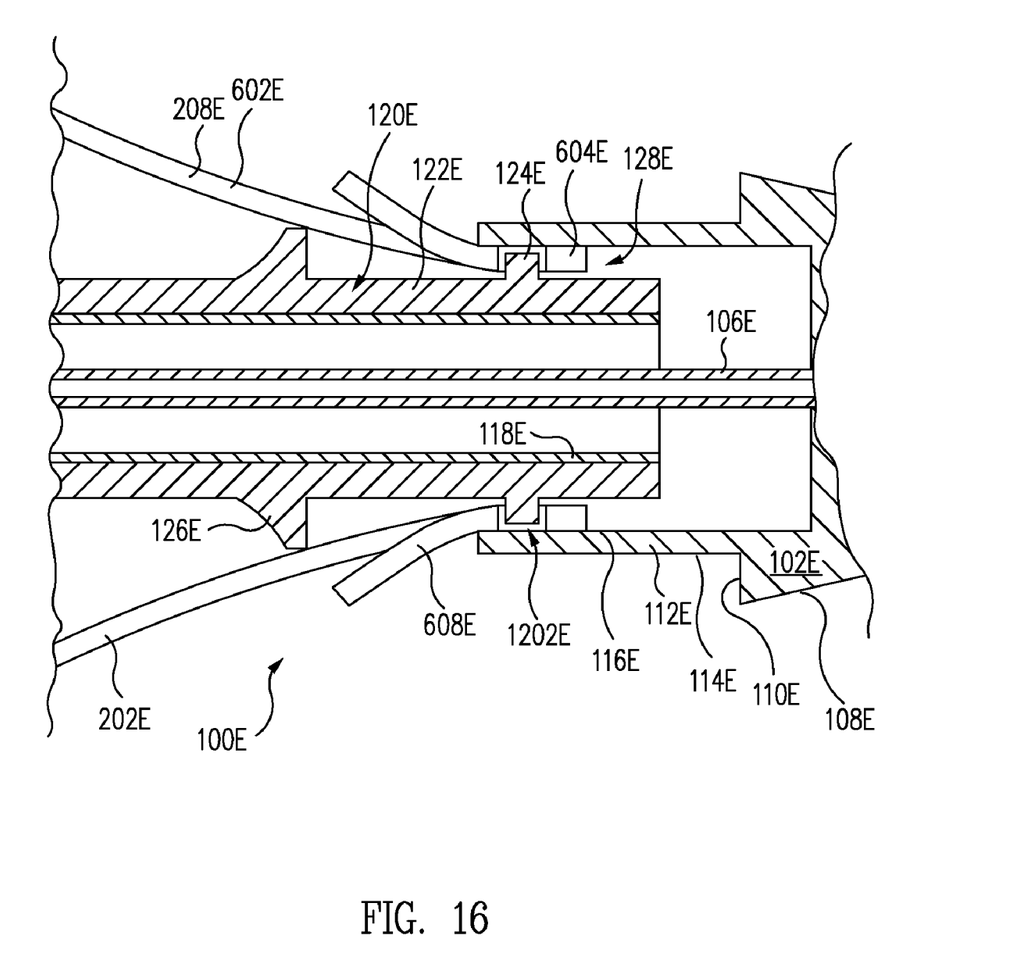
FIG. 16 is a cross-sectional view of the stent-graft delivery system of FIG. 15 at a further stage during deployment of a stent-graft.

FIG. 16 is a cross-sectional view of stent-graft delivery system 100E of FIG. 15 at a further stage during deployment of stent-graft 202E. Referring now to FIG. 16, tapered tip 102E and thus sleeve 112E are advanced relative to spindle 120E. However, as spindle pins 124E are still located within sleeve 112E, the proximal end of proximal anchor stent ring 208E continues to be locked around spindle pins 124E and between sleeve 112E and spindle body 122E.

Figure 17:
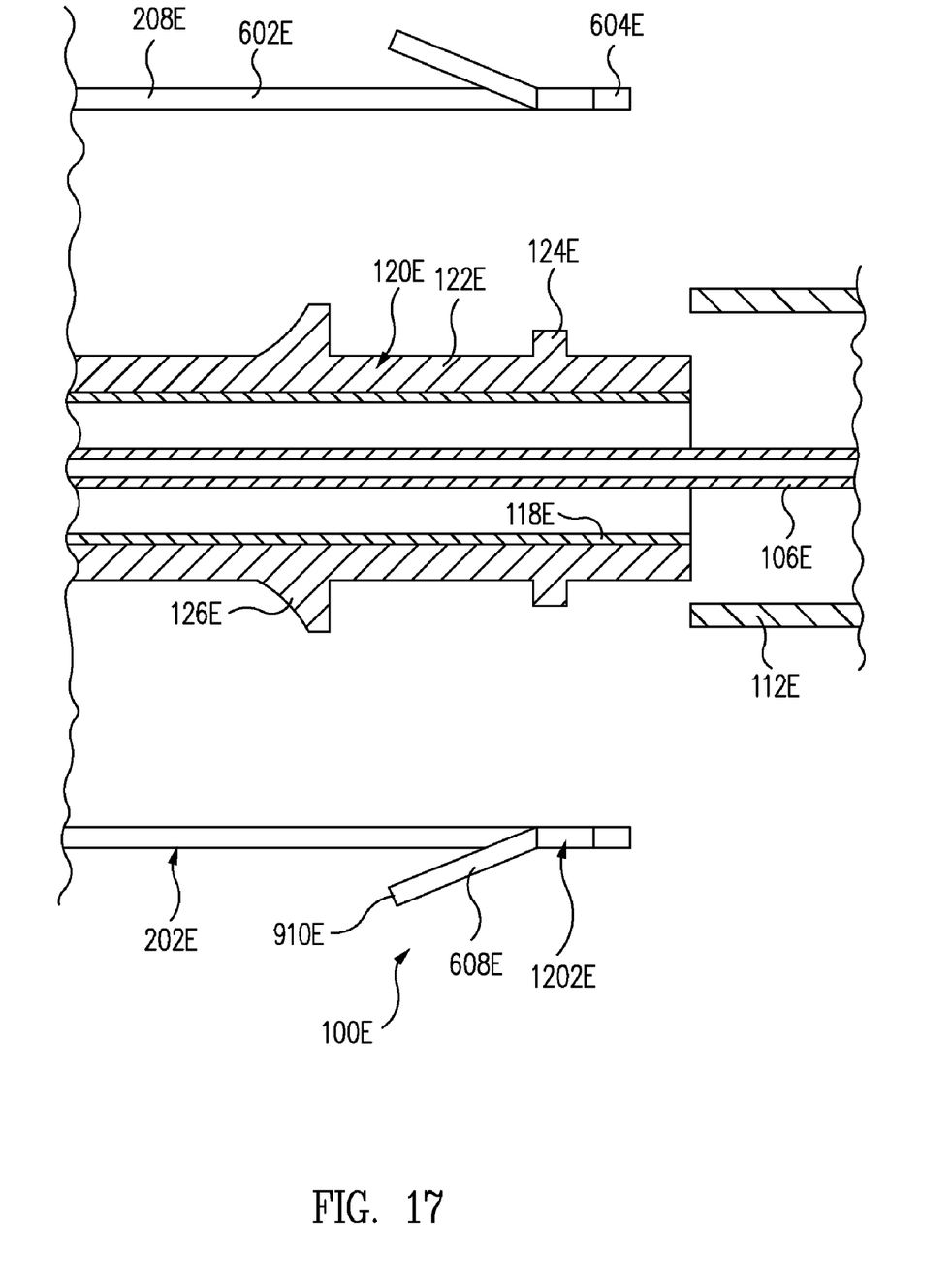
FIG. 17 is a cross-sectional view of the stent-graft delivery system of FIG. 16 at a final stage during deployment of the stent-graft.

FIG. 17 is a cross-sectional view of stent-graft delivery system 100E of FIG. 16 at a final stage during deployment of stent-graft 202E. FIG. 17 corresponds to the stage of deployment of stent-graft 202E similar to that illustrated in FIG. 4, i.e., after the proximal end of the proximal anchor stent ring has been deployed.

Referring now to FIG. 17, tapered tip 102E and thus sleeve 112E are advanced relative to spindle 120E such that sleeve 112E uncovers and exposes spindle pins 124E and proximal apexes 604E of proximal anchor stent ring 208E. Upon being released, proximal anchor stent ring 208E self-expands and anchors into the vessel wall, e.g., in a manner similar to that discussed above regarding FIG. 13.

Figure 18:
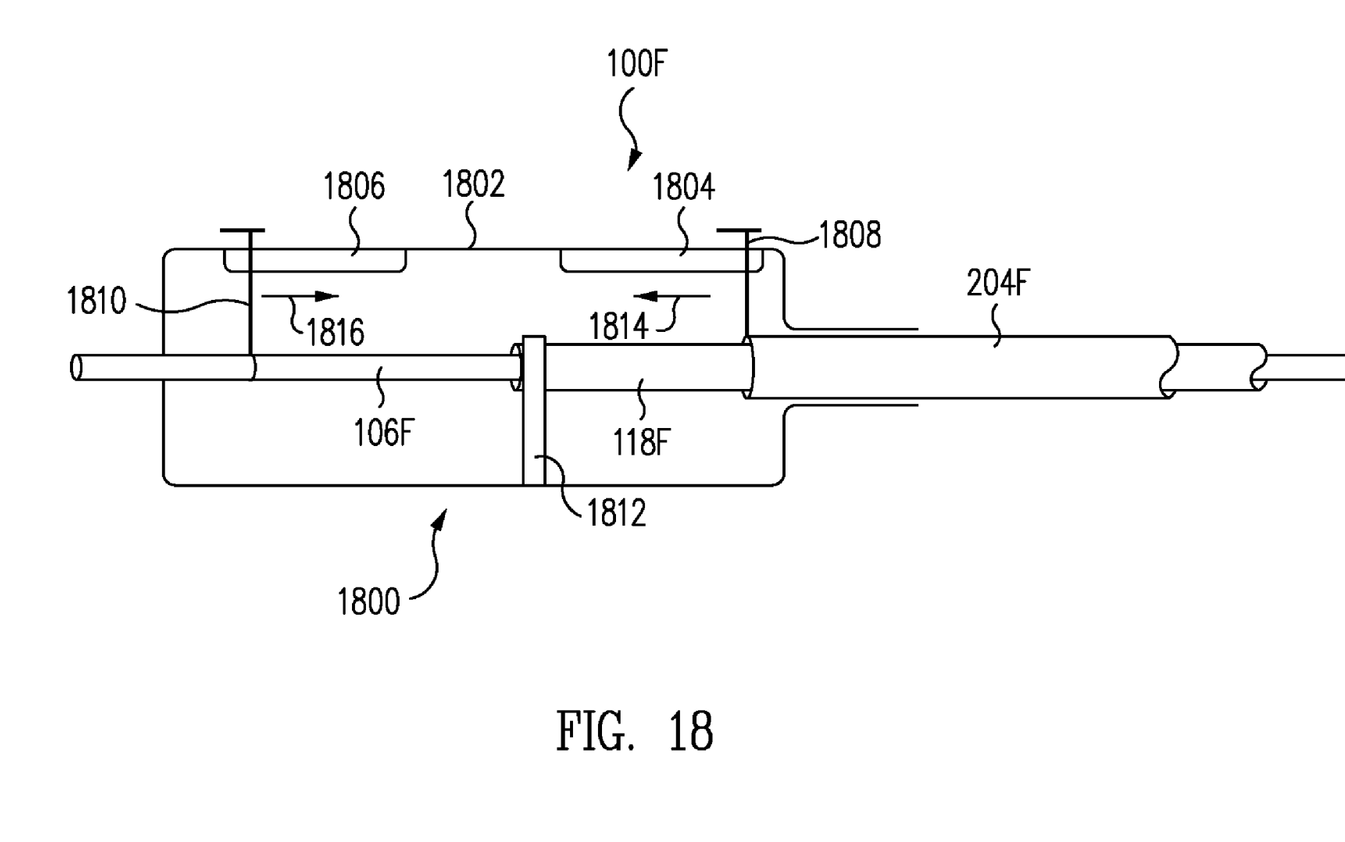
FIG. 18 is a handle of a stent-graft delivery system in accordance with one embodiment.

FIG. 18 is a handle 1800 of a stent-graft delivery system 100F in accordance with one embodiment. Handle 1800 includes a housing 1802 having a primary sheath retraction slot 1804 and an inner tube advancement slot 1806. A primary sheath actuation member 1808, sometimes called a thumb slider, extends from a primary sheath 204F and through primary sheath retraction slot 1804. Similarly, an inner tube actuation member 1810, sometimes called a thumb slider, extends from an inner tube 106F and through inner tube advancement slot 1806. Further, an outer tube 118F is mounted to housing 1802 by an outer tube support 1812.

To retract primary sheath 204F relative to outer tube 118F, primary sheath actuation member 1808 is moved (retracted), e.g., by the physician, in the direction of arrow 1814. To advance inner tube 106F relative to outer tube 118F, inner tube actuation member 1810 is moved (advanced), e.g., by the physician, in the direction of arrow 1816. Illustratively, inner tube 106F and outer tube 118F are stainless steel, Nitinol, MP35N alloy, or a braided polymer.

Although one example of a handle is set forth in FIG. 18, in light of this disclosure, those of skill in the art will understand that other handles can be used. Illustratively, handles having ratcheting mechanisms, threaded mechanisms, or other mechanisms to retract the primary sheath and advance the inner tube relative to the outer tube are used.

This application is related to Mitchell et al., co-filed and commonly assigned U.S. patent application Ser. No. 11/559,754, entitled "DELIVERY SYSTEM FOR STENT-GRAFT WITH ANCHORING PINS", which is herein incorporated by reference in its entirety.

The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

The invention claimed is:

1. An endoprosthesis comprising:
a proximal anchor stent ring comprising:
proximal apexes comprising a first proximal apex;
distal apexes;

struts extending between said proximal apexes and said distal apexes, wherein a first strut and a second strut of said struts extend distally from said first proximal apex; and anchor pins located on said struts adjacent said proximal apexes, said anchor pins comprising a first anchor pin extending from said first strut adjacent said first proximal apex and a second anchor pin extending from said second strut adjacent said first proximal apex and directly opposite said first anchor pin, wherein said first strut comprises an inside surface inward to a curvature of said first proximal apex, said first anchor pin extending inwards from said inside surface of said first strut, and wherein said second strut comprises an inside surface inward to said curvature of said first proximal apex, said second anchor pin extending inwards from said inside surface of said second strut, wherein said proximal apexes and said anchor pins define spindle pin catches comprising a first spindle pin catch defined by said first proximal apex, said first anchor pin, and said second anchor pin.

2. The endoprosthesis of claim 1 wherein a pair of said anchor pins is located on said struts adjacent each of said proximal apexes.

3. The endoprosthesis of claim 1 wherein said proximal anchor stent ring is integral.

4. The endoprosthesis of claim 3 wherein said proximal anchor stent ring is a single piece laser cut from a tube.

5. The endoprosthesis of claim 1 wherein an angle of said first anchor pin and said second anchor pin from vertical is in the range of 0° to 50°.

6. The endoprosthesis of claim 1 wherein an angle of said first anchor pin and said second anchor pin from vertical is 45°.

7. The endoprosthesis of claim 1 wherein said first proximal apex comprises an intrados surface continuous with said inside surface of said first strut and said inside surface of said second strut.

8. The endoprosthesis of claim 7 wherein said first strut further comprises an outside surface outward to said curvature of said first proximal apex, said outside surface of said first strut being proximal to said inside surface of said first strut, and wherein said second strut comprises an outside surface outward to said curvature of said first proximal apex, said outside surface of said second strut being proximal to said inside surface of said second strut.

9. The endoprosthesis of claim 8 wherein said first proximal apex further comprises an extrados surface continuous with said outside surface of said first strut and said outside surface of said second strut.

10. The endoprosthesis of claim 1 wherein said anchor pins comprise distal tips.

11. The endoprosthesis of claim 10 wherein said distal tips are sharp points.

12. The endoprosthesis of claim 1 wherein said anchor pins protrude radially outward from said struts of said proximal anchor stent ring.

13. The endoprosthesis of claim 12 wherein said anchor pins protrude radially outward from said struts of said proximal anchor stent ring a distance in the range of 1 mm to 3 mm.

14. The endoprosthesis of claim 12 wherein said anchor pins protrude radially outward from said struts of said proximal anchor stent ring a distance in the range of 2 mm to 3 mm.

15. The endoprosthesis of claim 12 wherein an angle of intersection between said anchor pins and said struts is in the range of 30° to 75°.

16. The endoprosthesis of claim 12 wherein an angle of intersection between said anchor pins and said struts is 45°.

17. The endoprosthesis of claim 1 wherein said struts, said proximal apexes, and said distal apexes define a cylindrical surface, said anchor pins protruding from said struts radially outward from said cylindrical surface.

18. The endoprosthesis of claim 1 wherein said spindle pin catches are pockets for spindle pins.

19. The endoprosthesis of claim 1 wherein said proximal anchor stent ring comprises super elastic self-expanding memory material.

20. The endoprosthesis of claim 1 further comprising a graft material attached to said proximal anchor stent ring.

21. The endoprosthesis of claim 20 further comprising support structures attached to said graft material, said support structures comprising said proximal anchor stent ring.

22. The endoprosthesis of claim 21 wherein said support structures further comprise a distal stent ring, and stent rings between said distal stent ring and said proximal anchor stent ring.

23. The endoprosthesis of claim 1 wherein said endoprosthesis comprises a stent-graft.

24. An endoprosthesis comprising:

a proximal anchor stent ring comprising:

proximal apexes comprising a first proximal apex;

distal apexes;

struts extending between said proximal apexes and said distal apexes, wherein a first strut and a second strut of said struts extend distally from said first proximal apex, wherein said struts, said proximal apexes, and said distal apexes define a cylindrical surface; and a pair of anchor pins located on said struts adjacent each of said proximal apexes, said anchor pins comprising a first anchor pin extending from said first strut adjacent said first proximal apex and a second anchor pin extending from said second strut adjacent said first proximal apex and directly opposite said first anchor pin, wherein said proximal apexes and said anchor pins define spindle pin catches comprising a first spindle pin catch defined by said first proximal apex, said first anchor pin, and said second anchor pin, said anchor pins extending inwards from inside surfaces of said struts and protruding from said struts radially outward from said cylindrical surface.

25. An endoprosthesis comprising:

a proximal anchor stent ring comprising:

proximal apexes comprising a first proximal apex;

distal apexes;

struts extending between said proximal apexes and said distal apexes, wherein a first strut and a second strut of said struts extend distally from said first proximal apex; and a pair of anchor pins located on said struts adjacent each of said proximal apexes, said anchor pins comprising a first anchor pin extending from said first strut adjacent said first proximal apex and a second anchor pin extending from said second strut adjacent said first proximal apex and directly opposite said first anchor pin, wherein said first strut comprises an inside surface inward to a curvature of said first proximal apex, said first anchor pin extending inwards from said inside surface of said first strut, and wherein said second strut comprises an inside surface inward to said curvature of said first proximal apex, said second anchor pin extending inwards from said inside surface of said second strut, said proximal apexes and said anchor pins defining spindle pin catches comprising a first spindle pin catch defined by said first proximal apex, said first anchor pin, and said second anchor pin, wherein said spindle pin catches are pockets for spindle pins.

* * * * *

UNITED STATES PATENT AND TRADEMARK OFFICE
CERTIFICATE OF CORRECTION

PATENT NO. : 7,655,034 B2 Page 1 of 1
APPLICATION NO. : 11/559765
DATED : February 2, 2010
INVENTOR(S) : Mitchell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 416 days.

Signed and Sealed this

Twenty-third Day of November, 2010

David J. Kappos
*Director of the United States Patent and Trademark Office*